| United States Patent [19] | [11] | 4,185,155 |
|---|---|---|
| Bader et al. | [45] | Jan. 22, 1980 |

[54] PRODUCTION OF ALKYL (ALKYLTHIO) CARBOXYLATES

[75] Inventors: Henry Bader, Newton; Susan J. Pavelko, Malden, both of Mass.

[73] Assignee: Polaroid Corporation, Cambridge, Mass.

[21] Appl. No.: 846,443

[22] Filed: Oct. 28, 1977

[51] Int. Cl.$^2$ .................. C07C 148/00; C07C 149/20
[52] U.S. Cl. .................................. 560/152; 260/399; 560/10; 560/15
[58] Field of Search .......................... 560/152, 15, 10; 260/399

[56] References Cited

U.S. PATENT DOCUMENTS

| 2,601,063 | 6/1952 | Smith et al. | 560/152 |
| 2,990,424 | 6/1961 | Guinot et al. | 560/152 |
| 3,758,549 | 9/1973 | Dexter et al. | 560/152 |

OTHER PUBLICATIONS

Carpenter et al., J. Chem. Soc., 2016, (1970).
Mooradian et al., J. Am. Chem. Soc., 71, 3372, (1949).
Chem. Abstracts, 7301c, (1957).

*Primary Examiner*—Vivian Garner
*Attorney, Agent, or Firm*—Esther A. H. Hopkins

[57] ABSTRACT

A process for an acid catalyzed esterification of a mercapto-carboxylic acid followed by an in situ S-alkylation of the mercapto-ester by slow addition of aqueous base to a mixture of said ester and an alkylating agent.

8 Claims, No Drawings

PRODUCTION OF ALKYL (ALKYLTHIO) CARBOXYLATES

This invention is concerned with a new preparation of alkyl (alkylthio) carboxylates useful in the preparation of 2-alkylthio-4,6-dihydroxypyrimidines. The use of 2-alkylthio substituted 4,6-dihydroxypyrimidines as silver halide solvents, i.e., silver halide complexing agents which form water soluble complex silver salts, is disclosed and claimed in Belgian Pat. No. 828,292 issued May 15, 1975. The 2-alkylthio substituted 4,6-dihydroxypyrimidines may be prepared by adding a malonamide to an alkyl (alkylthio) carboxylate as disclosed in the process of copending application of Bader and Sparks, Ser. No. 818,243 filed July 22, 1977, commonly assigned.

There are two relatively direct theoretical synthetic paths from a mercapto-acid

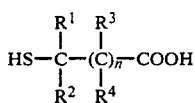

where $R^1$, $R^2$, $R^3$ and $R^4$ are individually hydrogen, methyl or ethyl and n is zero or an integer 1–4 to an alkyl (alkylthio) carboxylate

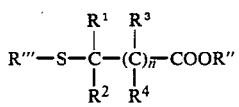

where R″ is a primary or secondary alkyl group with from four to twenty carbon atoms and R‴ is alkyl or aralkyl: one, a esterificaton followed by an alkylation and two, an alkylation followed by an esterification. Either path can present synthetic difficulties. In the first path the previously formed ester would be expected to undergo saponification during S-alkylation in the presence of aqueous alkali. The esters formed from these mercaptoacids are, in addition, noxious compounds and unpleasant to work with. In the second path, S-alkylation of a free acid is accompanied by a second S-alkylation with concomitant decarboxylation producing a dialkyl sulfide and carbon dioxide.

Carpenter and Shaw, J. Chem. Soc. 2016, (1970) prepared methyl (methylthio) acetate by methylating chilled preformed methyl thioglycolate in methanol which also contained sodium methoxide. Their medium was anhydrous, their yield for this second part of path one was 78%.

Mooradian et al, J. Amer. Chem. Soc. 71, 3372 (1949) alkylated a mercaptocarboxylic acid by adding an alkylating agent (diethyl sulfate) to a solution of the acid in aqueous sodium hydroxide. The yield over this first part of path two was 45%.

It is, therefore, the object of the present invention to provide an improved method for preparing alkyl (alkylthio) carboxylates from mercaptocarboxylic acids.

It is a further object of the present invention to provide a method of preparing alkyl (alkylthio) carboxylates in substantial yield from mercaptocarboxylic acids without isolating the noxious intermediate free mercaptoesters formed in the esterification of the mercaptocarboxylic acids.

Other objects of the invention will in part be obvious and will in part appear hereinafter.

The invention accordingly comprises the process involving the several steps and the relation and order of one or more of such steps with respect to each of the others which are exemplified in the following detailed disclosure, and the scope of the application of which will be indicated in the claims.

For a fuller understanding of the nature and objects of the invention, reference should be had to the following detailed description.

It has been discovered that alkyl (alkylthio) carboxylates can be formed in good yield from mercaptocarboxylic acids by esterification and subsequent alkylation in a one-pot synthesis if the esterification is driven to completion by removal of the water formed, the alkylating agent is added to the ester, and a strong aqueous base is then added to the ester/alkylating agent mixture at a slow rate so that S-alkylation of the mercaptide formed from the reaction of the base and the thiol takes precedence over either hydrolysis of the reagent or saponification of the ester group. Use of a solvent which forms an azeotrope with water allows azeotropic removal of the water formed and drives the esterification to completion. It is necessary to mix the alkylating agent into the ester before adding the strong aqueous base to direct the reaction of the base toward the formation of the mercaptide which reacts with the alkylating agent before the base can cause saponification of the ester grouping.

The mercaptoacids which are esterified and S-alkylated in the process of this invention have the general formula:

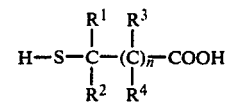

as noted above where each of $R^1$, $R^2$, $R^3$ and $R^4$ is hydrogen, methyl or ethyl and n is zero or an integer 1–4. The mercaptoacids have either straight or branched chains and include compounds of the following formulas:

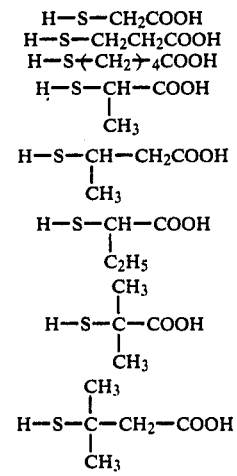

These thioacids are esterified by heating them in a medium comprising a suitable solvent and a strong acid catalyst with primary or secondary alcohols having from four to twenty carbon atoms such as, for example, 1-butanol, 3-pentanol, 1-hexanol, 1-octanol, benzyl alcohol and the like.

A suitable solvent is one which does not react with the reactants, the intermediates or the products. Preferred solvents for the process of this invention are liquids selected from the group consisting of liquid hydrocarbons and liquid halogenated hydrocarbons as, for example, toluene, benzene, chloroform and chlorobenzene. It is necessary that the solvent forms at least a binary azeotrope with water. Any ternary azeotrope formed should contain only minimal amount of the alcohol used for esterification. For example, the ternary azeotrope of benzene, 1-butanol, and water comprises 88.4 percent benzene, 10.1 percent water and 1.5 percent 1-butanol. The direct esterification of acids by alcohols with acid catalysts is well known. An ester and water are both formed. If the water is allowed to remain in the medium, the equilibrium is not shifted and all of the acid is not converted into the ester. Accordingly, all of the water is removed by azeotropic distillation.

After the water is removed, an alkylating agent containing an alkyl or aralkyl group, $R'''$, is added and then no more than one molar equivalent of a strong aqueous base is added at such a rate as to obtain substantially exclusive reaction between the hydroxide and the thiol to form a mercaptide which reacts with the alkylating agent. Two phases are formed. Examples of alkylating agents that may be used are, for example, methyl iodide, methyl p-toluenesulfonate, ethyl bromide, diethyl sulfate, dimethyl sulfate, benzyl bromide and isopropyl iodide. A preferred alkylating agent is dimethyl sulfate.

Examples of strong bases that may be used to initiate the reaction between the ester and the alkylating agent are alkali metal hydroxides such as, for example, sodium hydroxide, or alkaline earth hydroxides such as, for example, barium hydroxide. Excess of the strong base is to be avoided.

The unexpected high yields of S-alkylation realized in this process are related to the two-phase system, namely, the organic phase containing the intermediate ester and the alkylating agent, and the aqueous phase containing the strong base. Indeed under anhydrous conditions, for example, with alkali metal hydrides, lower yields of products are obtained. The use of nonaqueous bases such as alkali metal hydrides is not convenient and leads to foaming and frothing of the reaction medium.

After the S-alkylation, any excess alkylating agent is destroyed by quenching the reaction. In the preferred process using dimethyl sulfate this quenching may be done by stirring a tertiary amine such as triethylamine into the reaction medium.

Overall yields of the alkyl (alkylthio) carboxylates prepared by the instant process are better than 80% and approach 90% based on the mercaptoacid starting material.

The following examples have been presented for illustrative purposes only and are not intended to be in any way limiting.

EXAMPLE 1

Exactly 18.4 g (13.84 ml, 0.20 mol) of freshly distilled thioglycolic acid and 15.54 g (19.3 ml, 0.21 mol) of n-butanol were stirred with 120 ml of toluene containing about 0.03 g of sulfuric acid in a 500-ml flask equipped with a Dean-Stark distillation trap. The solution was refluxed for three hours for the azeotropic removal of about 3.6 ml of water. Upon cooling to 25°, the solution now containing n-butyl thioglycolate, was treated first with 27.72 g (20.9 ml, 0.22 mol) of dimethyl sulfate, followed by dropwise addition of 59 ml 3.525N sodium hydroxide with rapid stirring over a 45-min interval. The exotherm was controlled with an ice bath, keeping the temperature below 30°, and the end point of the addition of the aqueous sodium hydroxide was determined with the color change of phenolphthalein indicator. The two-phase system was then rapidly stirred for 15 minutes with 2.5 g (3.5 ml, 0.025 mol) of triethylamine to destroy any excess dimethyl sulfate. The lower aqueous phase was separated and the toluene layer washed with 100 ml of water. After separation, the resulting toluene solution was stripped under vacuum removing all traces of water to give an oily crude product. This oil was distilled uner vacuum to give 26.3 (83% yield) based on thioglycolic acid of pure n-butyl (methylthio) acetate, b.p. 78–80° (2.5 mm): IR (neat) 1725 cm$^{-1}$ anal. calculated for $C_7H_{14}O_2S$: C,51.82; H,8.70; S,19.76 Found: C,52.18; H,8.72; S,20.49.

EXAMPLE 2

The reaction of Example 1 was repeated using 23.0 g of 80% thioglycolic acid in place of the 18.4 g of freshly distilled thioglycolic acid. The pure n-butyl (methylthio) acetate formed weighed 27.6 g, an 87% yield based on thioglycolic acid.

Since certain changes may be made in the above process without departing from the scope of the invention herein involved, it is intended that all matter contained in the above description shall be interpreted as illustrative and not in a limiting sense.

What is claimed is:

1. A process which comprises the following steps:
esterifying a mercaptocarboxylic acid of the formula

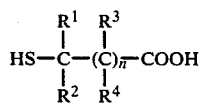

where each of $R^1$, $R^2$, $R^3$, and $R^4$ is hydrogen, methyl or ethyl and n is zero or an integer 1–4, with a primary or secondary alcohol of the formula $R''OH$, where $R''$ is a primary or secondary alkyl group with from 4–20 carbon atoms, by heating said acid in a medium comprising a suitable solvent and a strong acid catalyst, said solvent being capable of forming an azeotrope with water, to form an alkyl mercaptocarboxylate of the formula

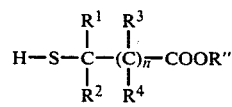

and water,
removing said water by azeotropic distillation from said medium substantially as said water is formed, adding an alkylating agent containing $R'''$ where $R'''$ is alkyl or aralkyl, and thereafter
adding no more than a molar equivalent of an aqueous strong base to the mixture of said alkyl mercaptocarboxylate and said alkylating agent at such a rate that said alkyl mercaptocarboxylate forms a mercaptide in preference to being saponified, reacting said mercaptide with said alkylating agent, whereby an alkyl (alkylthio) carboxylate of the formula

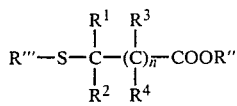

is formed.

2. The process of claim 1 wherein said alcohol is 1-butanol.

3. The process of claim 1 wherein said alkylating agent is selected from the group consisting of dimethyl sulfate, methyl iodide, diethyl sulfate, methyl p-toluenesulfonate, ethyl bromide, benzyl bromide and isopropyl iodide.

4. The process of claim 1 wherein said base is selected from the group consisting of alkali metal hydroxides and alkaline earth hydroxides.

5. The process of claim 4 wherein said base is sodium hydroxide.

6. The process of claim 1 wherein said solvent is selected from the group consisting of liquid hydrocarbons and liquid halogenated hydrocarbons.

7. The process of claim 6 wherein said solvent is toluene.

8. A process which comprises esterifying mercaptoacetic acid with 1-butanol in a solution of toluene in the presence of an acid catalyst to form n-butyl mercaptoacetate and water, removing said water azeotropically substantially as said water is formed, adding dimethylsulfate to said solution, and adding no more than a molar equivalent of aqueous sodium hydroxide at a rate such that S-methylation can occur, whereby n-butyl (methylthio) acetate is formed.

* * * * *